(12) United States Patent
Erdmann et al.

(10) Patent No.: US 10,475,540 B2
(45) Date of Patent: Nov. 12, 2019

(54) IMPACTABILITY SCORING

(71) Applicant: CERNER INNOVATION, INC., Kansas City, KS (US)

(72) Inventors: Cole Anthony Erdmann, Kansas City, MO (US); Darcy Davis, Elmhurst, IL (US)

(73) Assignee: CERNER INNOVATION, INC., Kansas City, KS (US)

( * ) Notice: Subject to any disclaimer, the term of this patent is extended or adjusted under 35 U.S.C. 154(b) by 460 days.

(21) Appl. No.: 14/930,400

(22) Filed: Nov. 2, 2015

(65) Prior Publication Data
US 2016/0125158 A1 May 5, 2016

Related U.S. Application Data

(60) Provisional application No. 62/074,265, filed on Nov. 3, 2014.

(51) Int. Cl.
*G16H 50/30* (2018.01)
*G16H 10/60* (2018.01)
*G06F 19/00* (2018.01)

(52) U.S. Cl.
CPC ............. *G16H 50/30* (2018.01); *G06F 19/00* (2013.01); *G16H 10/60* (2018.01)

(58) Field of Classification Search
CPC ... G06F 11/3058; G06F 19/30; A61B 5/0022; A61B 5/746; A61B 5/0205; A61B 5/002; A61B 5/053; A61B 5/0816; G06Q 50/24
See application file for complete search history.

(56) References Cited

U.S. PATENT DOCUMENTS

2003/0065534 A1* 4/2003 McCartney ........... G06F 19/328
705/2
2012/0191469 A1* 7/2012 Akradi ................... G06Q 50/22
705/2
2016/0042135 A1* 2/2016 Hogan ................... G16H 50/20
705/2

* cited by examiner

*Primary Examiner* — Reginald R Reyes
(74) *Attorney, Agent, or Firm* — Shook, Hardy & Bacon L.L.P.

(57) ABSTRACT

Methods, systems, and computer-readable media for creating a model that enables a health system with a population of patients to better understand its patient population by being able to track which patients are being well-managed and which patients may be in need of some type of clinical intervention are provided. The methods, systems, and computer-readable media create a model that enables a health system to assess its patient population in terms of wellness, complexity, and impactability. Wellness provides a measure of resource consumption of patients within the population, complexity measures the long-term complexity of patients within the population, and impactability provides an indication of how in-need a patient is of some type of clinical intervention.

16 Claims, 5 Drawing Sheets

IMPACTABILITY SCORING

CROSS-REFERENCE TO RELATED APPLICATIONS

This Non-Provisional Patent Application claims the benefit of U.S. Provisional Patent Application No. 62/074,265, filed Nov. 3, 2014 and titled "IMPACTABILITY SCORING," the teachings of which are incorporated herein by reference in their entirety.

BACKGROUND

Health systems utilize a variety of models when looking at the population of patients for which they provide care. One typical model is a stratification of the patient population based on risk and/or cost. Risk, in turn, may be based on, for example, a number of disease conditions associated with a particular patient. This type of model may be useful if a health system is attempting to determine how much it will spend on patient care in the upcoming year. However, these types of models may not be useful for identifying patients that may need some type of clinical intervention, nor are they useful for identifying what type of intervention is needed. As an example, under traditional models, a patient may be suffering from multiple, chronic disease conditions and thus be considered a "high-risk" patient that has a high cost of care. However, this patient may be well-managed and therefore not in need of any type of clinical intervention. Current models fail to make this distinction.

SUMMARY

This summary is provided to introduce a selection of concepts in a simplified form that are further described below in the detailed description section. This summary is not intended to identify key features or essential features of the claimed subject matter, nor is it intended to be used as an aid in determining the scope of the claimed subject matter. The present invention is defined by the claims.

In brief, and at a high level, this disclosure describes, among other things, methods, systems, and computer-readable media for creating a model that enables a health system with a population of patients to better understand its patient population by being able to track which patients are being well-managed and which patients may be in need of some type of clinical intervention. As used throughout this disclosure, the term "intervention" or "clinical intervention" means a point of contact of the patient with the health system. As such, the term is meant to be broad and encompass any type of contact between the patient and the health system caring for the patient.

The model takes into account wellness scores, complexity scores, and impactability scores for each patient in the population. Wellness scores may provide a measure of a particular patient's "wellness" in terms of resource consumption relative to the health system's patient population that share similar levels of complexity, while complexity scores may provide a measure of the long-term complexity of the particular patient. The patient's impactability score may be generated based on the patient's wellness and complexity scores and provides an indication of how "in need" the patient is to some type of clinical intervention. For example, a high impactability score may indicate that the patient is in need of some type of clinical intervention, while a low impactability score may indicate that the patient is being well-managed and is not in need of a clinical intervention.

BRIEF DESCRIPTION OF THE DRAWINGS

Embodiments are described in detail below with reference to the attached drawings figures, wherein.

DETAILED DESCRIPTION

Figure 1:
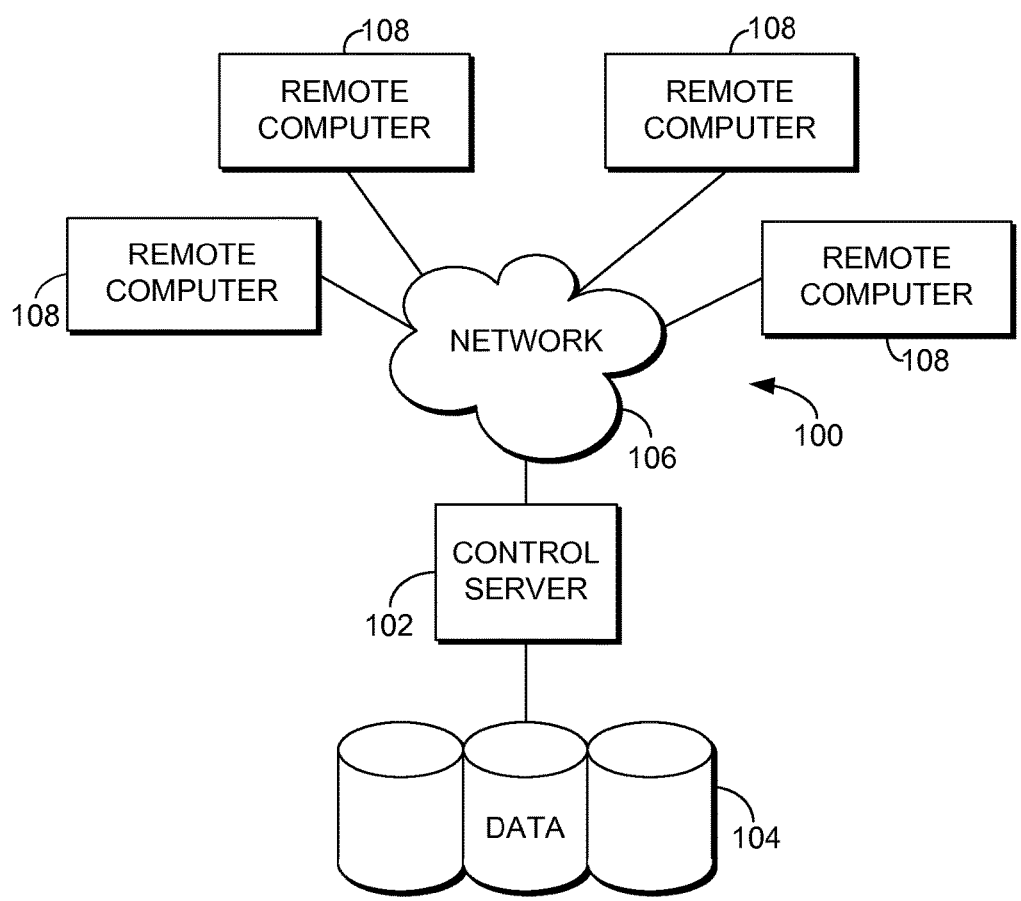
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different elements of methods employed, the terms should not be interpreted as implying any particular order among or between various steps herein disclosed unless and except when the order of individual steps is explicitly described.

Embodiments of the present invention are directed to methods, systems, and computer-readable media for creating a model that enables a health system to assess its patient population in terms of wellness, complexity, and impactability. Wellness provides a measure of resource consumption of patients within the population, complexity measures the long-term complexity of patients within the population, and impactability provides an indication of how in need a patient is of some type of clinical intervention.

More specifically, aspects described herein are directed to generating wellness scores for each patient in the patient population, complexity scores for each of the patients, and impactability scores for each of the patients. A patient's wellness score is generated by taking a variety of wellness parameters for the patient and training them towards an estimated paid cost-of-care during a specified period of time. Wellness parameters may comprise: 1) clinical measures of wellness such as vital signs associated with the patient, labs, tests, and procedures associated with the patient, and the like; 2) resource consumption indicators such as a number and type of patient encounters with the health system, medications utilized, durable home health equipment utilized, and the like; and 3) quality of life indicators (such as in the form of patient surveys, ambulation status, patient support system, and the like).

A patient's complexity score is calculated based on disease condition sets associated with the patient and reflects an average expected cost-of-care for patients having that particular condition set. It is calculated independently of any labs, procedures, or demographic data (excepting age, as age is considered a type of chronic condition) associated with the patient. A patient's complexity score takes into account that combinations of certain disease conditions (e.g., condition sets) do not necessarily increase patient care costs proportional to each disease condition by itself. This is because certain labs, tests, services, and/or procedures may be shared between certain disease conditions, and, thus, would only be ordered once. For example, the disease conditions of Diabetes Mellitus Type II and hypertension commonly occur together and similar lab tests are shared by each.

In aspects, for a population of patients, each patient's wellness and complexity scores may be plotted on a graph with the y-axis representing complexity and the x-axis representing wellness. The resulting scatter plot reflects the wellness and complexity scores for all, or a designated subset of the patients within a population. Further, the graph may further comprise a middle axis originating at (0, 0) and representing the average wellness and complexity scores for the patient population. Such a graph may be displayed to a clinician on a user interface, where it is useable by the clinician to quickly assess his/her patient population in terms of wellness and complexity. The graph may also provide a visual representation of the distribution of needs and costs within the patient population, and enables the comparison of patient groups among physicians.

Continuing, a patient's impactability score is calculated by taking the difference between the patient's wellness and complexity scores, and, when this value is positive, dividing the difference by the number of standard deviations from the average wellness score for the population of patients having the same complexity score as the patient (as represented by the middle axis on the graph). As will be explained in more depth below, a patient having a large impactability score is considered in high need of some type of clinical intervention. These patients typically have high wellness scores indicating a high amount of medical resource consumption as compared to other patients having the same condition set as the patient in question. By instituting clinical intervention measures for patients with large impactability scores, the patient's impactability score may decline and the patient's wellness may move more towards the average (e.g., move towards a more average resource consumption or cost-of-care for that particular condition set).

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multi-processor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of non-transitory computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like, and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keypad, a microphone (e.g., voice inputs), a touch screen, a pointing device (commonly referred to as a mouse), a trackball, and/or a touch pad. Other input devices comprise satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
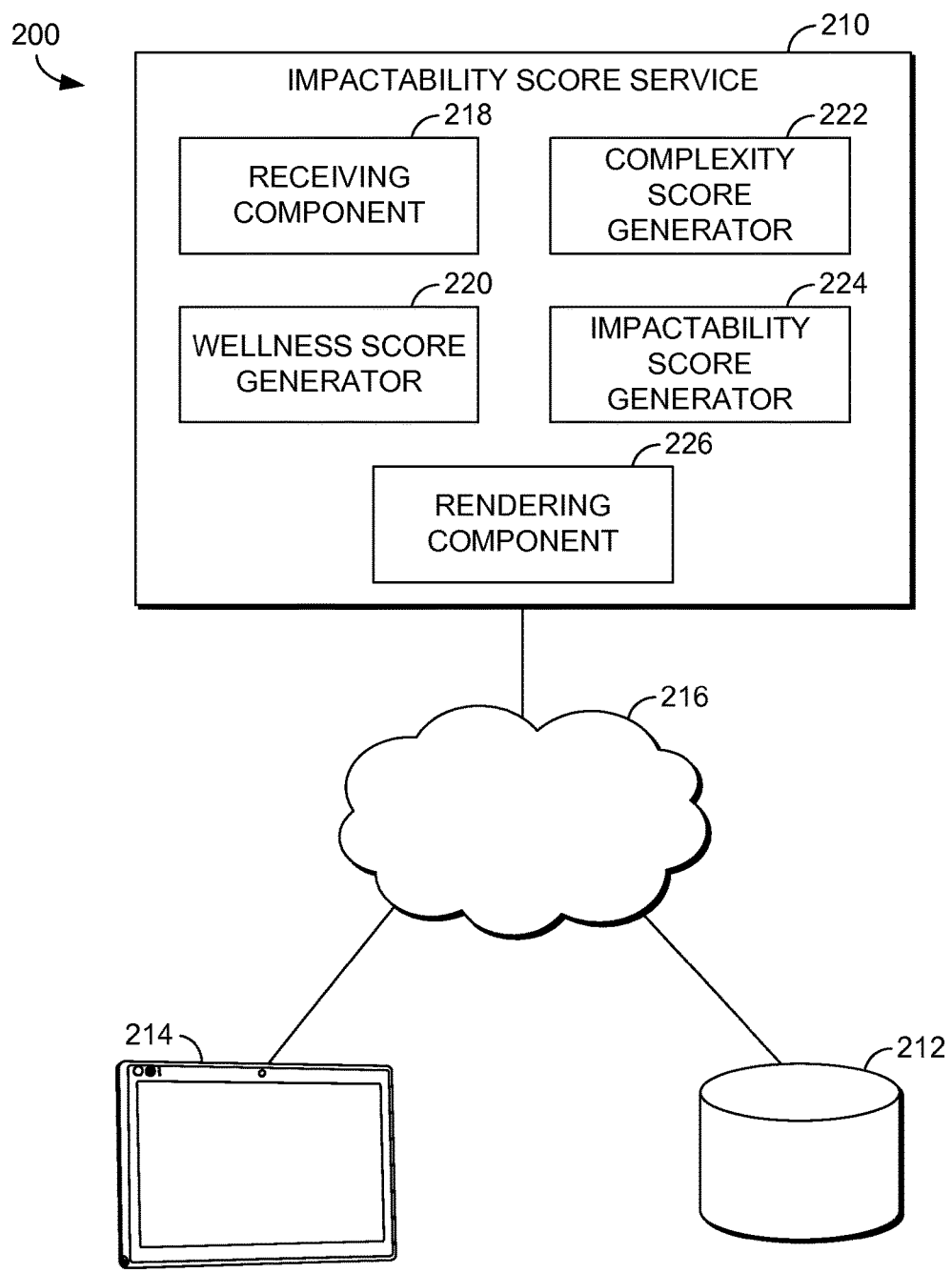
FIG. 2 is a block diagram showing an exemplary architecture for generating impactability scores for patients suitable to implement embodiments of the present invention.

Turning now to FIG. 2, an exemplary computing system environment 200 is depicted suitable for use in implementing embodiments of the present invention. The computing system environment 200 is merely an example of one suitable computing system environment and is not intended to suggest any limitation as to the scope of use or functionality of embodiments of the present invention. Neither should the computing system environment 200 be interpreted as having any dependency or requirement related to any single module/component or combination of modules/components illustrated therein.

The computing system environment 200 includes an impactability score service 210, a data store 212, and an end-user computing device 214, all in communication with each other via a network 216. The network 216 may include, without limitation, one or more local area networks (LANs) or wide area networks (WANs). Such networks are commonplace and, as such, will not be further described herein.

In some embodiments, one or more of the illustrated components/modules may be implemented as stand-alone applications. In other embodiments, one or more of the illustrated components/modules may be integrated directly into the operating system of the impactability score service 210. Moreover, the impactability score service 210 may be integrated directly into the operating system of the end-user computing device 214. The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, the impactability score service 210 might reside on a server, a cluster of servers, or a computing device remote from one or more of the remaining components.

The computing system environment 200 is merely exemplary. While the impactability score service 210 is illustrated as a single unit, it will be appreciated that the impactability score service 210 is scalable. For example, the impactability score service 210 may in actuality include a plurality of computing devices in communication with one another. Moreover, the data store 212, or portions thereof, may be included within, for instance, the impactability score service 210 as a computer-storage medium. The single unit depictions are meant for clarity, not to limit the scope of embodiments in any form.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The data store 212 is configured to store information for use by, for example, the impactability score service 210. The information stored in association with the data store 212 is configured to be searchable for one or more items of information stored in association therewith. The information stored in association with the data store 212 may comprise general information used by the impactability score service 210.

The data store 212 may store a variety of information. In an exemplary aspect, the data store 212 may store electronic medical records (EMRs) of patients associated with a healthcare facility or health system. EMRs may comprise electronic clinical documents such as images, clinical notes, survey results, orders, summaries, reports, analyses, and/or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, patient-entered information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, diagnoses, condition sets, billing information, immunizations, physician comments, nurse comments, other caretaker comments, and a host of other relevant clinical information.

The data store 212 may also store reference information which may include decision protocols, differential diagnoses lists, condition-specific intervention measures, reference tables, best practice information, and the like. The information may be provided by, for example, third-party content providers, and/or the information may be promulgated by, for example, different health systems utilizing the impactability score service 210. Reference information may include, for instance, expected costs or average costs associated with different disease condition sets.

The content and volume of such information in the data store 212 are not intended to limit the scope of embodiments of the present invention in any way. Further, though illustrated as a single, independent component, the data store 212 may, in fact, be a plurality of storage devices, for instance, a database cluster, portions of which may reside on the impactability score service 210.

As shown, the end-user computing device 214 includes a display screen. The display screen is configured to display information to the user of the end-user computing device 214, for instance, information relating to wellness scores, complexity scores, impactability scores, and suggested intervention measures for a patient population. Embodiments are not intended to be limited to visual display but rather may also include audio presentation, combined audio/visual presentation, and the like. The end-user computing device 214 may be any type of display device suitable for presenting information. Such computing devices may include, without limitation, a computer, such as, for example, any of the remote computers 108 described above with reference to FIG. 1, mobile devices, tablet devices, and the like. Interaction with the end-user computing device 214 may be via a touch pad, a microphone, a pointing device, and/or gestures.

As shown in FIG. 2, the impactability score service 210 comprises a receiving component 218, a wellness score generator 220, a complexity score generator 222, an impactability score generator 224, and a rendering component 226. In some embodiments, one or more of the components 218, 220, 222, 224, and 226 may be implemented as stand-alone applications. In other embodiments, one or more of the components 218, 220, 222, 224, and 226 may be integrated directly into the operating system of a computing device such as the end-user computing device 214. It will be understood that the components 218, 220, 222, 224, and 226 illustrated in FIG. 2 are exemplary in nature and in number and should not be construed as limiting. Any number of components may be employed to achieve the desired functionality within the scope of embodiments hereof.

The receiving component 218 is configured to receive a variety of inputs/requests and access a variety of parameters from, for instance, the data store 212. For example, the receiving component 218 is configured to receive user requests, such as user requests for wellness scores, complexity scores, and/or impactability scores. The receiving component 218 is also configured to receive user selections, such as a selection of wellness, complexity, and impactability scores for a particular population segment of interest. For instance, the user may be clinician Dr. Smith, and Dr. Smith may be interested in viewing wellness, complexity, and impactability scores for just those patients that Dr. Smith treats.

The receiving component 218 is also configured to access a variety of patient information from the data store 212. The information may comprise wellness parameters as well as condition sets for each patient in the patient population. Wellness parameters for a particular patient may comprise, for instance, vital signs, labs, tests, procedures, number and type of health system visits, medication utilization, quality of life indicators, and the like. And condition sets include a grouping of all the conditions associated with a particular patient.

The wellness score generator 220 is configured to generate a wellness score for each patient in the patient population. A patient's wellness score reflects or approximates the patient's resource consumption and quality of life. As used throughout this disclosure, resource consumption may be defined as the type and quantity of healthcare resources consumed by the patient. This may include health system visits or stays such as emergency department visits, nursing home stays, clinic visits, doctor visits, and the like, as well as medication utilization, durable medical equipment utilization, and the like. This is expressed numerically as an estimated cost-of-care.

The wellness score generator 220 generates each patient's wellness score by utilizing the wellness parameters received by the receiving component 218 and training them using a model to an estimated paid cost-of-care. Training may be done by employing a random subspace ensemble with regression trees as the base classifier, each employing 10-fold cross-validation. The output of the model is a value or score. The wellness score generator 220 may refit the values to fit on a 0 to 100 continuous scale.

The complexity score generator 222 is configured to generate a complexity score for each patient in a patient population. As mentioned, the complexity score comprises a measure of the long-term complexity associated with a patient and is determined based on condition sets associated with the patient. Condition sets comprise all of the diagnosed disease conditions associated with the patient. The complexity score generator 222 considers age as a "disease condition" and, thus, this is factored in as well. Importantly, the complexity score generator 222 only considers diagnoses sets and age and does not take into account other types of data associated with the patient such as, for example, labs, procedures, and/or demographic data.

Once the condition sets are determined for the patient, the complexity score generator 222 may reference the data store 222 which contains a reference table listing known condition sets and associated average costs-of-care. Thus, the complexity score for a patient reflects the average cost-of-care for the condition set associated with the patient. The average cost-of-care for different condition sets takes into account that costs-of-care for some conditions that occur together is actually lower than if the cost-of-care for each disease condition were added together. This is because some disease conditions share similar testing, procedures, office visits, and the like.

For those patients with large condition sets, the complexity score generator 222 is configured to take the largest condition set that has an average cost-of-care associated with it and add a margin of error to this value. For those patients who have a rare condition on which average cost-of-care data is not available, the complexity score generator 222 is configured to search for a close relative of the patient (e.g., parent, sibling, cousin, etc.) and determine if a complexity score is associated with the relative. If so, the patient will be assigned this complexity score. In general, a patient's complexity score remains relatively stable unless the patient is diagnosed with a new condition.

The impactability score generator 224 is configured to utilize patient wellness and complexity scores and generate an impactability score for each of the patients in the patient population. The impactability score generator 224 does this by subtracting the patient's complexity score from the patient's wellness score and, if the result is positive, dividing that value by the number of standard deviations away from the average wellness score for people having the same complexity score as the patient (i.e., the patient's z-score). Mathematically this may be expressed by the following formula:

$$\frac{\text{Wellness Score} - \text{Complexity Score}}{\text{Patient's Z-score}} = \text{Impactability Score}$$

As stated, this calculation is only carried out when the difference between the patient's wellness score and complexity score is a positive number. This reflects the fact that patients with high wellness scores relative to their complexity scores are consuming more resources than expected based on the particular complexity of the patient.

At a high level, an impactability score describes the patient's wellness (i.e., resource consumption) relative to other patients in the patient population that share the same complexity level as the patient. It is generally based on the concept that patients who are statistically less well (e.g., have a higher impactability score) should be more impactable. In other words, for two patients who share the same condition set, the patient who is less well or has the higher impactability score is more in need of some type of clinical intervention than the patient with the lower impactability score. This type of situation may occur, for example, when a patient is being non-compliant with his/her medications, is missing office visits, is failing to perform self-monitoring, is on the wrong medications, has been wrongly diagnosed, and the like.

The impactability score generator 224 may be further configured to determine one or more intervention measures for a patient when the patient's impactability score exceeds some predefined threshold. This may be done by, for instance referencing the patient's electronic medical record (EMR) along with reference materials to determine an appropriate intervention measure. The impactability score generator 224 is further configured to determine healthcare personnel best-suited to carry out the intervention measure. As an illustrative example, upon determining that a patient's impactability score exceeds a predefined threshold set by, for example, the health system caring for the patient, the patient's EMR is accessed. The patient's EMR indicates that the patient has missed several clinic appointments and has not been reporting the results of a self-monitoring program. Based on this, the impactability score generator 224 may determine that the patient should be enrolled in care management services where a care manager works closely with the patient to make sure that appointments are attended and self-monitoring is accomplished. In another example, after determining that a patient's impactability score is greater than a predefined threshold, the impactability score generator 224 accesses the patient's EMR and determines that the patient is taking the wrong medication for his/her particular condition set. This determination may be carried out by utilizing the reference information stored in the data store 212. Based on this, the impactability score generator 224 may send a notification to the patient's primary care physician notifying the physician of the determination and possibly suggesting a new medication for the patient. These are just illustrative examples, and many other examples are contemplated as being within the scope herein.

The impactability score generator 224 is also configured to stratify patients with a patient population based on their respective impactability scores. Patient with higher scores are those in greater need of an intervention than those with lower impactability scores. This information may be graphically presented using, for example, the rendering component 226.

Figure 3:
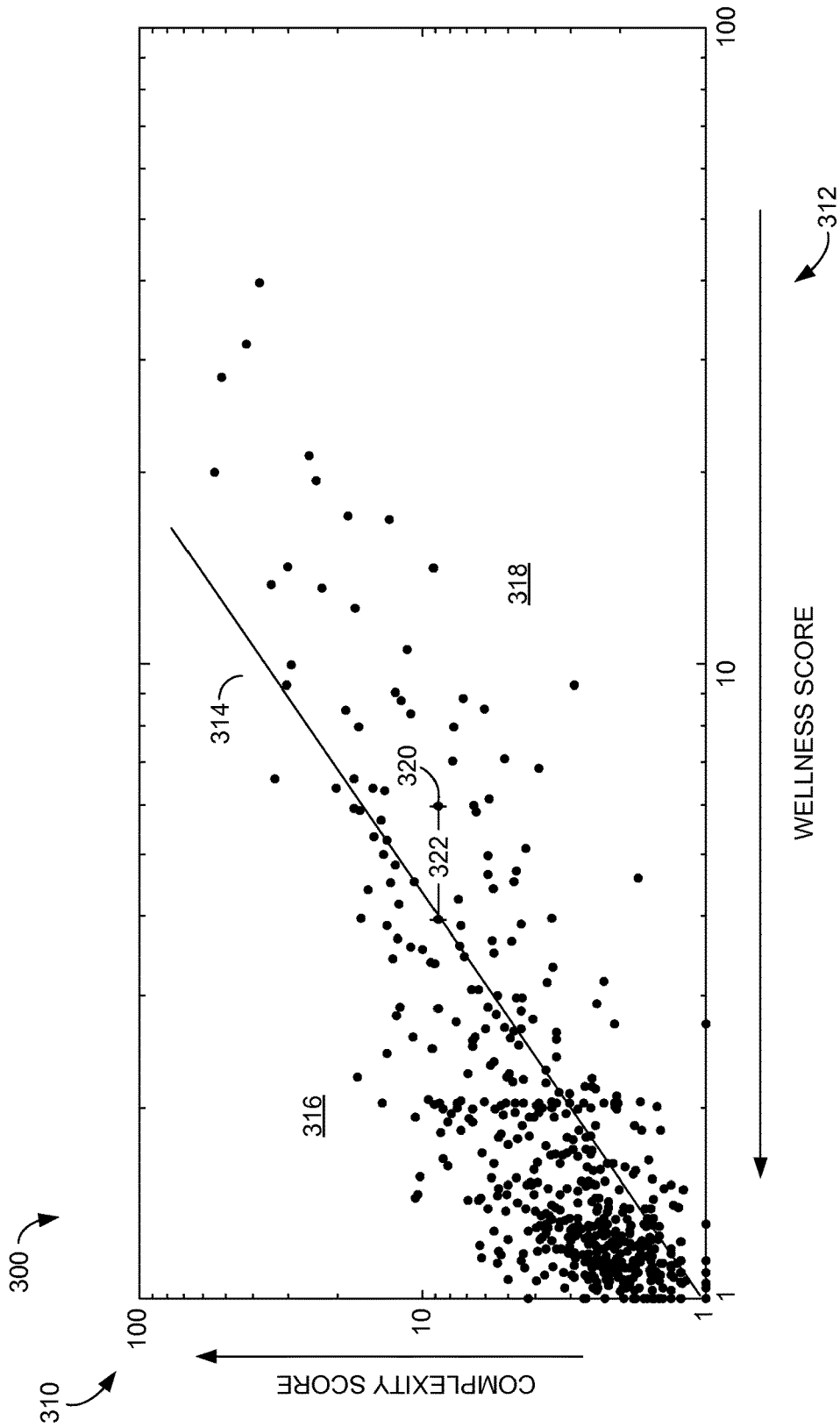
FIG. 3 depicts an illustrative relationship between wellness and complexity for patients in a patient population, in accordance with an embodiment of the present invention.

The rendering component 226 is configure to use the complexity scores, the wellness scores, and the impactability scores and generate one or more graphs, tables, and the like that may be displayed on a user interface of a display device such as the end-user computing device 214. Such graphical representations may be used by, for example, healthcare providers caring for one or more of the patients, the health system caring for the patient population, and the like. An exemplary scatter plot graph is shown in FIG. 3 and is referenced by the numeral 300. The graph 300 has complexity scores 310 plotted on the y-axis and expressed in average cost, and wellness scores 312 plotted on the x-axis and expressed as estimated cost. With respect to complexity scores, a complexity score of 0 indicates that the patient has essentially no conditions or condition sets. Similarly, a wellness score of 0 indicates that the patient is perfectly well (e.g., has no resource utilization). Thus, as a patient's wellness score increases (as you move to the right on the graph 300), the patient's resource utilization increases. The result is that a patient with a high wellness score paradoxically has more resource consumption than a patient with a low wellness score.

Continuing, each point in the graph 300 represents a patient within the health system's patient population. Filters may be available that enable a user to select certain population segments for viewing. Exemplary filters may comprise filtering by physician, healthcare facility, geographic region, disease condition, and the like. The graph 300 further includes a middle axis 314 that represents the average wellness and complexity scores for the patient population. The middle axis 314 divides the graph into two regions: 316 and 318. Those patients in the area 316 (e.g., above and to the left of the middle axis 314) generally represent patients who are currently well-managed. In other words, patients in the area 316 have generally low wellness scores, indicating low resource utilization even though the patients may have high complexity scores. By contrast, patients in the area 318 (e.g., below and to the right of the middle axis 314) generally represent patients who are less well-managed for whatever reason. To put it another way, patients in the area 318 generally have high wellness scores even though the patients may have low complexity scores. Of course, the further a patient in area 318 is horizontally from the middle axis 314, the higher the patient's wellness score is compared to people with similar complexity scores and the more the patient is in need of intervention.

As described, each patient is represented by a point on the graph 300. The different points may be, for example, color-coded to represent different characteristics such as gender, age, geographic location, provider caring for the patient, and the like. Other ways of characterizing the points are contemplated herein such as, for example, configuring the shape of the point to indicate certain characteristics. Each point, in addition, may be actionable. For example, hovering over or selecting a particular point may reveal additional information about the patient represented by the point such as, for example, the patient's impactability score, patient identifying information, condition sets associated with the patient, and the like. Taking point 320 in particular, as shown point 320 is a distance 322 from the middle axis 314. The patient represented by the point 320 would have an impactability score determined by taking the distance 322 and dividing it by the number of standard deviations from the middle axis 314.

Figure 4:
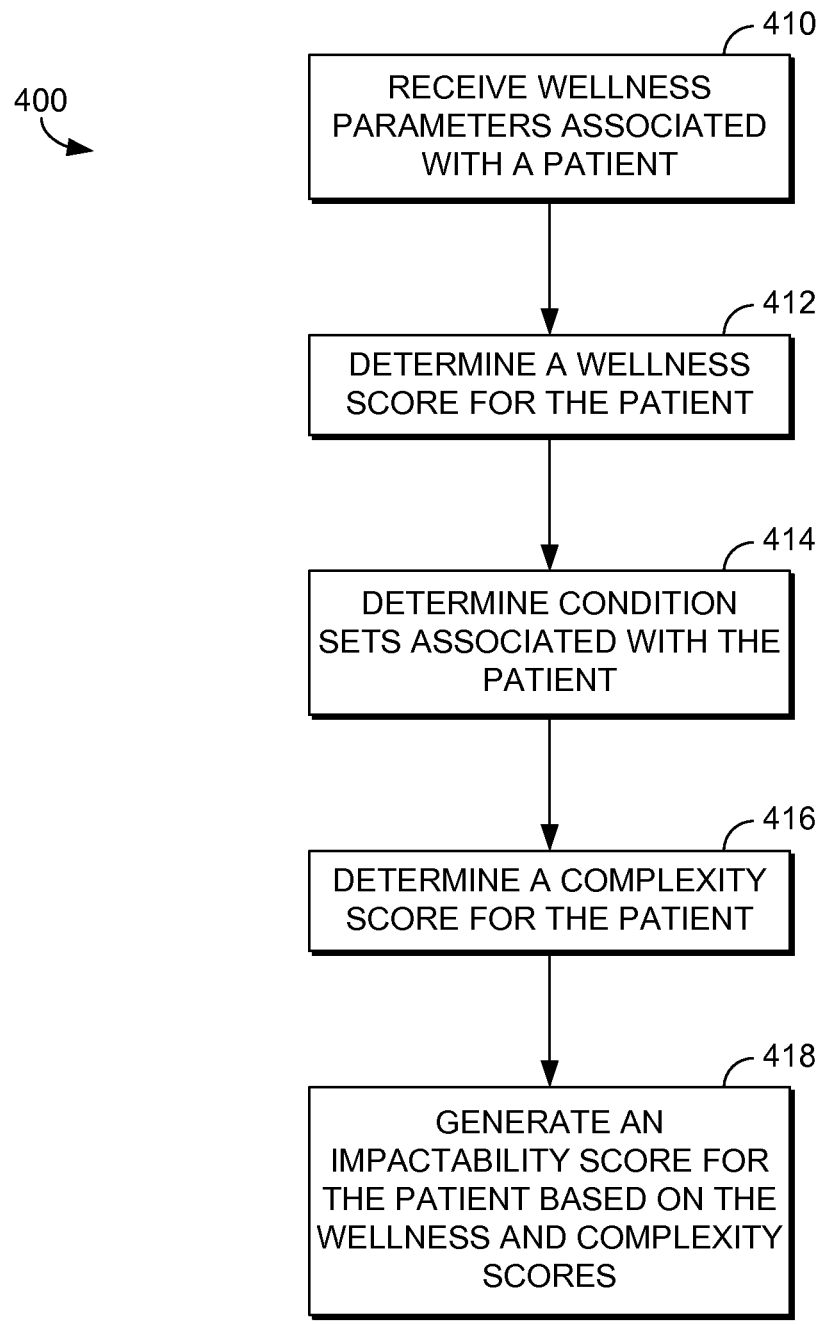
FIG. 4 is a flow diagram illustrating an exemplary method of generating an impactability score for a patient in a patient population, in accordance with an embodiment of the present invention.

Turning now to FIG. 4, a flow diagram is depicted of an exemplary method 400 of generating an impactability score for a patient within a patient population, in accordance with an embodiment of the present invention. At a step 410, wellness parameters may be received by a receiving component such as the receiving component 218 of FIG. 2. The wellness parameters may be accessed from the patient's EMR and comprise such things as vital signs, labs, tests, procedures, patient encounters with the health system, medication and durable home health equipment utilization, and quality of life indicators, among other things.

At a step 412, the wellness parameters are trained toward an estimated cost-of-care by a wellness score generator, such as the wellness score generator 220 of FIG. 2. The wellness score represents an estimated amount of resource utilization based on the patient's wellness parameters and is typically expressed as a numerical value between 0 and 100.

At a step 414, a complexity score generator, such as the complexity score generator 222 of FIG. 2, determines condition sets associated with the patient by, for instance, accessing the patient's EMR. The patient's condition set may also be determined based on insurance claims data for the patient. At a step 416, the complexity score generator may determine a complexity score for the patient by, for example, accessing a reference table mapping condition sets to average cost-of-care, locating the patient's condition set in the reference table, and determining the average cost-of-care for that particular condition set.

At a step 418, an impactability score is determined for the patient using the patient's complexity score and wellness score. This is accomplished by an impactability score generator such as the impactability score generator 224 of FIG. 2. In aspects, the impactability score may be generated by subtracting the patient's complexity score from the wellness score, and, if this number is positive, dividing the difference by the number of standard deviations (i.e., the Z-score) away from the average wellness score for that particular complexity score.

The method 400 may further comprising communicating for presentation on a display device the patient's wellness score, complexity score, and impactability score. This may be carried out by a rendering component such as the rendering component 226 of FIG. 2 and may comprise, for example, a graphical representation such as the graph 300 of FIG. 3.

Figure 5:
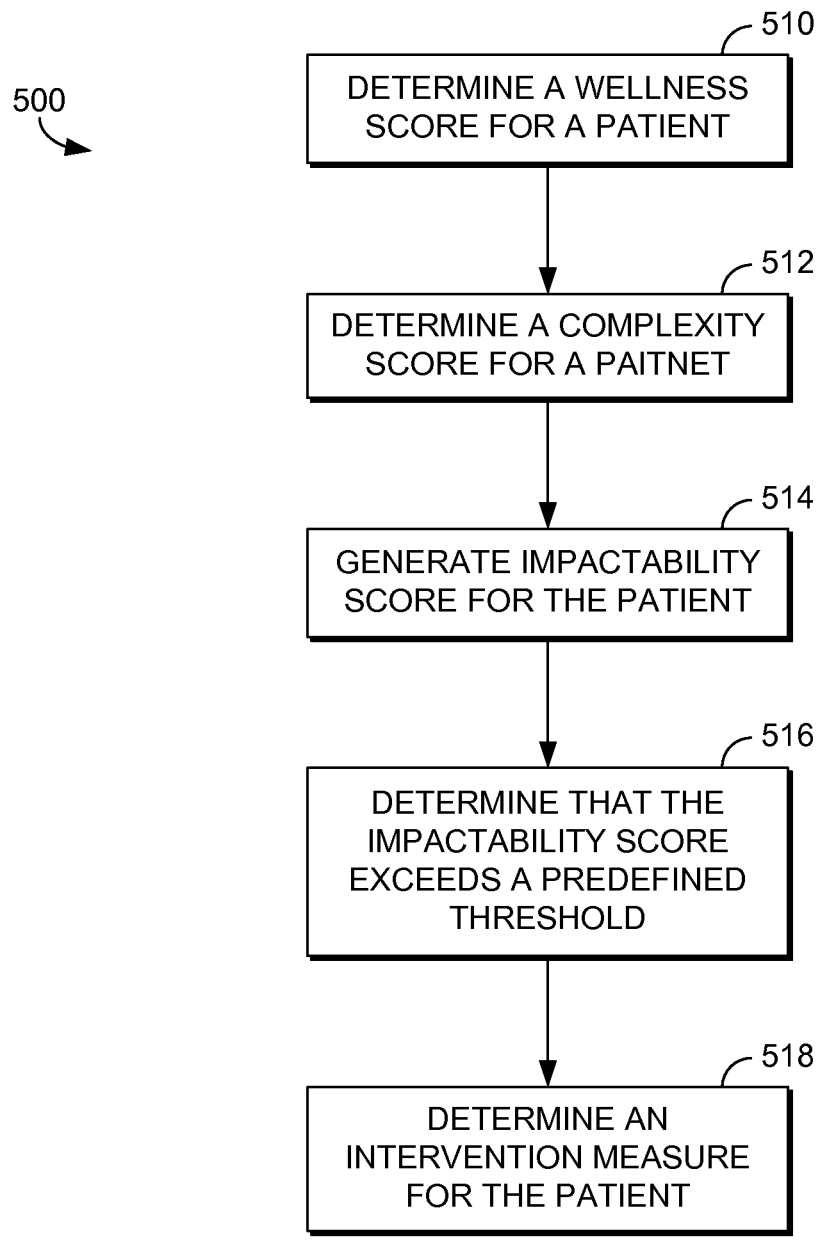
FIG. 5 is a flow diagram illustrating an exemplary method of generating an impactability score for a patient and determining an intervention measure for the patient, in accordance with an embodiment of the present invention.

FIG. 5 depicts a flow diagram of an exemplary method 500 of generating an impactability score for a patient and using the impactability score to determine an appropriate clinical intervention for the patient, in accordance with an embodiment of the present invention. At a step 510, a wellness score is determined for the patient using the patient's wellness parameters. This process is similar to steps 410 and 412 of the method 400. At a step 512, a complexity score is determined for the patient similar to steps 414 and 416 of the method 400. At a step 514, an impactability score is determined for the patient similar to step 418 of the method 400.

At a step 516, it is determined that the patient's impactability score exceeds a predefined threshold. The threshold may be set by a health system, a provider caring for the patient, and the like. At a step 518, and incident to determining that the impactability score exceeds the predefined threshold, an intervention measure is determined for the patient. This may be carried out by an impactability score generator such as the impactability score generator 224 of FIG. 4. The intervention measure may be determined by analyzing clinical data in the patient's EMR, and utilizing reference materials such as decision algorithms, and/or other sources of data. In one aspect, determining an intervention measure includes determining healthcare personnel suited to carry out the intervention measure. For instance, if the intervention measure comprises some type of clinical order, a physician may be selected. If the intervention measure comprises some type of care management service, a care manager may be selected. Additionally, if the intervention measure comprises some type of change to the patient's medication schedule, a pharmacist and the patient's physician may be selected. The method 500 may further comprise sending a notification to the selected personnel informing him/her of the patient's impactability score along with the suggested intervention.

The present invention has been described in relation to particular embodiments, which are intended in all respects to be illustrative rather than restrictive. Further, the present invention is not limited to these embodiments, and variations and modifications may be made without departing from the scope of the present invention.

What is claimed is:

1. A computerized method, carried out by at least one server having one or more processors, of generating impactability scores for a population of patients, the method comprising:

receiving a plurality of wellness parameters for a patient in the population of patients, the wellness parameters comprising one or more of vital signs, labs, procedures, a number and type of patient encounters, and an indication of medication utilization;

generating, using the one or more processors, a wellness score for the patient using the plurality of wellness parameters, the wellness score comprising an indication of an amount of resource utilization associated with the patient; determining a condition set associated with the patient, the condition set comprising a plurality of diagnosed disease conditions associated with the patient;

generating a complexity score for the patient based on the condition set, the complexity score comprising an indication of the long-term complexity of the patient;

using at least the wellness score and the complexity score to calculate an impactability score for the patient, the impactability score comprising an indication of whether a clinical intervention for the patient is needed;

determining that the impactability score exceeds a predefined threshold;
determining one or more intervention measures are needed for the patient; and
instituting the one or more clinical intervention measures for the patient.

2. The method of claim 1, where the plurality of wellness parameters further comprise one or more quality of life indicators.

3. The method of claim 1, wherein generating the wellness score comprises training the plurality of wellness parameters to an estimated cost-of-care.

4. The method of claim 1, wherein the wellness score comprises a score between 0 and 100.

5. The method of claim 4, wherein a value associated with the wellness score is inversely proportional to the amount of resource utilization associated with the patient.

6. The method of claim 1, wherein determining the condition set associated with the patient comprises accessing the patient's electronic medical record (EMR) and determining a number of disease conditions documented for the patient.

7. The method of claim 1, wherein determining the complexity score for the patient comprises:
accessing a reference table that maps condition sets to average cost-of-care;
locating the patient's condition set in the reference table; and
determining an average cost-of-care associated with the patient's condition set.

8. The method of claim 1, wherein the complexity score comprises a score between 0 and 100.

9. The method of claim 1, wherein calculating the impactability score for the patient comprises:
subtracting the patient's complexity score from the patient's wellness score;
determining that the result is positive; and
dividing the result by a number of standard deviations between the patient's wellness score and an average wellness score for patients having the same complexity score as the patient.

10. The method of claim 1, further comprising generating a graphical representation of the patient's wellness score, complexity score, and impactability score.

11. One or more computer-readable media having computer-executable instructions embodied thereon that, when executed by a computing device, perform a method of determining a clinical intervention for a patient based on the patient's impactability score, the method comprising:
determining a wellness score for the patient based on one or more parameters comprising vital signs, labs, procedures, a number and type of patient encounters, and an indication of medication utilization;
determining a complexity score for the patient based on a condition set associated with the patient;
generating an impactability score for the patient based at least upon the patient's wellness score and complexity score;
determining that the impactability score exceeds a predefined threshold;
determining an intervention measure for the patient; and
instituting the intervention measure for the patient.

12. The media of claim 11, wherein the wellness score is further determined based on one or more quality of life indicators.

13. The media of claim 11, wherein the predefined threshold is configurable by a healthcare provider associated with the patient.

14. The media of claim 11, wherein the predefined threshold is configurable by a health system caring for the patient.

15. The media of claim 11, wherein determining an intervention measure for the patient further comprises determining healthcare personnel to implement the intervention measure.

16. The media of claim 15, further comprising communicating the intervention measure to the healthcare personnel.

* * * * *